United States Patent
Liu

(10) Patent No.: US 9,089,168 B2
(45) Date of Patent: Jul. 28, 2015

(54) ELECTRONIC CIGARETTE

(71) Applicant: Qiuming Liu, Guangdong (CN)

(72) Inventor: Qiuming Liu, Guangdong (CN)

(73) Assignee: HUIZHOU KIMREE TECHNOLOGY CO., LTD. SHENZHEN BRANCH, Shenzhen (CN)

( * ) Notice: Subject to any disclaimer, the term of this patent is extended or adjusted under 35 U.S.C. 154(b) by 0 days.

(21) Appl. No.: 14/098,060

(22) Filed: Dec. 5, 2013

(65) Prior Publication Data

US 2015/0053218 A1    Feb. 26, 2015

(30) Foreign Application Priority Data

Aug. 22, 2013    (CN) .................. 2013 2 0520036 U

(51) Int. Cl.
*A24F 47/00* (2006.01)
*A61M 15/06* (2006.01)

(52) U.S. Cl.
CPC ............. *A24F 47/008* (2013.01); *A24F 47/002* (2013.01); *A61M 15/06* (2013.01)

(58) Field of Classification Search
CPC ..... A24F 47/002; A24F 47/008; A61M 15/06
USPC .............................. 131/237, 329; 128/202.21
See application file for complete search history.

(56) References Cited

U.S. PATENT DOCUMENTS

| 2009/0126745 | A1* | 5/2009  | Hon ............................ 131/273 |
| 2013/0319438 | A1* | 12/2013 | Liu ............................. 131/329 |
| 2013/0340778 | A1* | 12/2013 | Liu ............................. 131/329 |
| 2014/0150785 | A1* | 6/2014  | Malik et al. ............. 128/202.21 |
| 2015/0059786 | A1* | 3/2015  | Li et al. ..................... 131/329 |

OTHER PUBLICATIONS

Litetronics, Light Bulb Bases Guide Part 2: Pin Bases [downloaded online from archive.org], Oct. 13, 2010 [downloaded on Nov. 24, 2014].*
Amazon.com, Lighting Ever 5W GU10 LED Bulbs [downloaded from amazon.com], downloaded on Nov. 24, 2014.*

* cited by examiner

*Primary Examiner* — Anthony Calandra
(74) *Attorney, Agent, or Firm* — Locke Lord LLP; Tim Tingkang Xia, Esq.

(57) ABSTRACT

The electronic cigarette comprises a battery assembly and an atomizer assembly; the battery assembly and the atomizer assembly are connected to each other through a first connector and a second connector. The first connector comprises a first top electrode and a second top electrode mounted on an end face of the first connector. The second connector comprises a first bottom electrode and a second bottom electrode located in the second connector. When the battery assembly and the atomizer assembly are connected together, there are elastic tight fit occurred between the first top electrode and the first bottom electrode as well as between the second top electrode and the second bottom electrode.

12 Claims, 5 Drawing Sheets

ELECTRONIC CIGARETTE

CROSS-REFERENCE TO RELATED APPLICATIONS

This non-provisional application claims priority under 35 U.S.C. §119(a) on Patent Application No. 201320520036.3, filed in P.R. China on Aug. 22, 2013, the entire contents of which are hereby incorporated by reference.

FIELD OF THE INVENTION

The present invention relates to the technical field of electronic-heating technology, and more particularly relates to an electronic cigarette.

BACKGROUND OF THE UTILITY MODEL

Because domestic publicity of anti-smoking and the people's awareness of health are enhanced, electronic cigarettes, which serve as the substitute of traditional tobacco, have been more and more widely used. An existing electronic cigarette comprises a battery assembly and an atomizer assembly connected to the battery assembly. The battery assembly is provided with a battery. The atomizer assembly is provided with a heating wire, an ultrasonic atomizer or the like. The atomizer assembly and the battery are electrically connected to each other. The atomizer assembly is provided with an external thread, and the battery assembly is provided with an internal thread. Therefore, the atomizer assembly and the battery assembly are connected to each other in thread connection. However, with such connection manner, the atomizer assembly and the battery assembly may be offset with respect to each other. The connection between the atomizer assembly and the battery assembly in such manner may be relaxed easily with poor reliability and bad users' feel.

SUMMARY OF THE INVENTION

Aiming at the drawbacks in the prior art that the battery assembly and the atomizer assembly are easy to be offset with respect to each other and connected inconveniently. An electronic cigarette that the battery assembly and the atomizer assembly can connect to each other reliably and conveniently is provided in the disclosure.

In accordance with one aspect of the present application, there is provided an electronic cigarette, which comprises a battery assembly and an atomizer assembly, the battery assembly and the atomizer assembly are connected to each other through a first connector and a second connector, wherein, the first connector comprises a first top electrode and a second top electrode mounted on an end face of the first connector and extending in the direction toward the second connector along an axial direction of the first connector, wherein the first top electrode and the second electrode are arranged parallelly and spaced from each other; wherein, the second connector comprises a first bottom electrode and a second bottom electrode that are located in the second connector, when the battery assembly and the atomizer assembly are connected together, there are elastic tight fit occurred between the first top electrode and the first bottom electrode as well as between the second top electrode and the second bottom electrode, and, the first top electrode and the first bottom electrode are connected electrically to each other, and the second top electrode and the second bottom electrode are connected electrically to each other; during assembling, the first top electrode is inserted into the first bottom electrode and the second top electrode is inserted into the second bottom electrode, then both the first and second bottom electrodes are expanded and produce elastic deformation so that the atomizer assembly is connected to the battery assembly in the form of elastic tight fit to obtain an electric power from the battery assembly. The first top electrode, the second top electrode, the first bottom electrode and the second bottom electrode are made of elastic conductive material that can expand or contract in the radial direction of the electrodes. The elastic conductive material is elastic metal. Preferably, the first and second top electrode are of columnar shape, wherein, the first bottom electrode is shaped to match the first top electrode, and the second bottom electrode is shaped to match the second top electrode respectively. Preferably, cross sections of the first and second top electrode are round-shaped or oval-shaped. Preferably, the first connecter further comprises an first installation base for fixing the first and second top electrodes, the first installation base defines a pair of first installation hole for the installation of the first and second top electrodes, and a first breathing hole is formed between the pair of the first installation holes. Preferably, the second connector further comprises a second installation base, the second installation base defines a pair of second installation holes for the installation of the first and second bottom electrodes, and a second breathing hole is formed between the pair of the second installation holes, the first breathing hole and the second breathing hole communicate with each other to form a channel for cigarette smoke flowing. Preferably, the first and second installation bases are made of insulated material. Preferably, the atomizer assembly is provided with a first outer tube and the battery assembly is provided with a second outer tube, the first connector or the second connector are mounted at one end of the first outer tube or the second outer tube respectively, the first outer tube is detachably connected to the second outer tube through the connection between the first connector and the second connector.

In one embodiment, cross sections of the first and second top electrodes are round-shaped, wherein each of the first and second top electrodes comprises a top part, a fixing part and a connecting part, wherein the fixing part is connected to the first connector and the connecting part is connected between the top part and the fixing part. A diameter of the connecting part is less than that of the top part and the fixing part, and a ring-shaped groove is formed on an outer surface of the connecting part. The first and second bottom electrodes are of the same shape. Each of the first and second bottom electrodes comprise an engaging part extending in the direction toward the first connector and a second connecting part received in the second connector; wherein, the engaging part includes a plurality of plates arranged radially in the circumferential direction of the engaging part; a protruding part that can expand or contract along the radial direction of the engaging part is formed on each plate along the radial direction of the engaging part; all of the protruding parts surround to form a block button for engaging with the ring-shaped groove.

In another embodiment, cross sections of the first and second top electrodes are round-shaped, wherein, each of the first and second top electrodes comprise a top part, a fixing part and a connecting part, wherein the fixing part is connected to the first connector and the connecting part is connected between the top part and the fixing part. The connecting part comprises a plurality of protruding strip and a slot formed between each two adjacent protruding strip, wherein a diameter of the connecting part is more than that of the top part. The first and second bottom electrodes are hollow cylinder shaped, and the diameter of the first and second bottom electrodes are equal to that of the top parts of the first and second top electrodes. The first and second top electrodes are made of elastic metal.

When implementing the invention, the following advantages can achieve:

In this disclosure, the atomizer assembly is connected to the battery assembly by means of elastic tight fit occurred between the top electrodes and the bottom electrodes respectively. In such case, the atomizer assembly and the battery assembly can be connected to each other conveniently with less force. While connecting, users only need to insert the atomizer assembly into the battery assembly. In such case, the atomizer assembly and the battery assembly can be connected to each other reliably, which can bring with a good users' feel.

BRIEF DESCRIPTION OF THE DRAWINGS

The present disclosure can be further illustrated by reading the example with references made to the accompanying drawings, in which.

DETAILED DESCRIPTION OF THE PREFERRED EMBODIMENT

In this disclosure, there is provided a connection way of elastic tight fit between an atomizer assembly and a battery assembly in an electrical cigarette.

Figure 1:
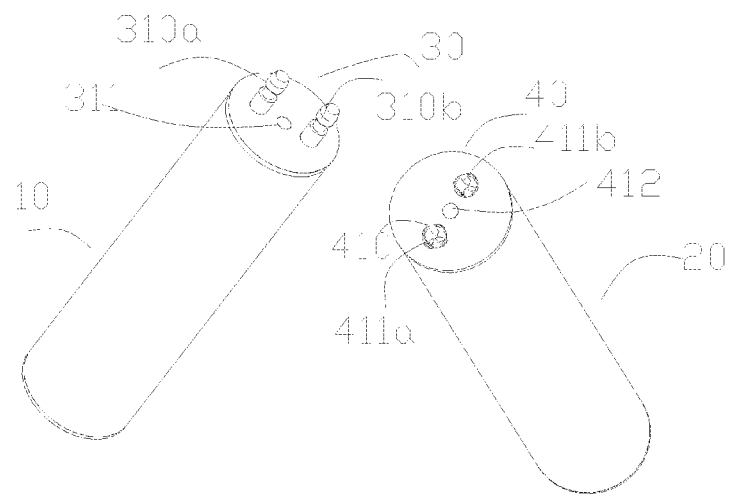
FIG. 1 is a stereoscopic view of an electronic cigarette in accordance with the disclosure.

As shown in FIG. 1, an electronic cigarette in this disclosure comprises a battery assembly 10 and an atomizer assembly 20. A first connector 30 and a second connector 40 are separately disposed at the atomizer assembly 20 and the battery assembly 10. The battery assembly 10 and the atomizer assembly 20 are connected to each other by means of a connection between the first connector 30 and the second connector 40.

Figure 2:
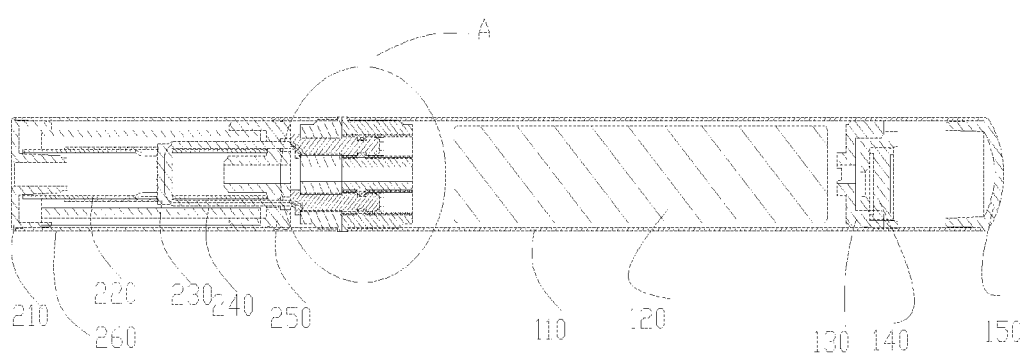
FIG. 2 is a cutaway view of an electronic cigarette in accordance with one embodiment of the disclosure.

As shown in FIG. 2, the battery assembly 10 comprises a second outer tube 110, an end cover 150, a control module 130, a fixing base 140, a battery 120 and second connector 40. The second outer tube 110 is hollow cylinder shaped. The second connector 40 is mounted at one end of the second outer tube 110, The end is closed to the atomizer assembly 20. The end cover 150 covers another end of the second outer tube 110; the end is away from the atomizer assembly 20. The fixing base 140, the control module 130 and the battery 120 that are received in the inner of the second outer tube 110 are mounted between the end cover 150 and the second connector 40 in orderly. Preferably, the end cover 150, the second connector 40 and the second outer tube 110 are formed integrally as one piece. In other embodiments, the end cover 150 and the second connector 40 are connected to the second outer tube 110 respectively in interference fit connection, engagement connection, or the like.

The atomizer assembly 20 comprises a suction mouth cover 210, a first outer tube 260, a breathing pipe 220, a heating device 230, a storing means 240, a sealing base 250 and a first connector 30. The first outer tube 260 is hollow cylinder shaped. The first connector 30 is mounted at one end of the first outer tube 260, the end is closed to the battery assembly 10. The suction mouth cover 210 is engaged with another end of the first outer tube 260; the end is away from the battery assembly 10. Preferably, the suction mouth cover 210, the first outer tube 260 and the first connector 30 are formed integrally as one piece. In other embodiments, the suction mouth cover 210 and the first connector 30 are connected to the first outer tube 260 respectively in interference fit connection, engagement connection, or the like. The breathing pipe 220 and the sealing base 250 configured for sealing the breathing pipe 220 are mounted in the inner of the first outer tube 260 in orderly, particularly mounted between the suction mouth cover 210 and the first connecting means 30. A cavity (not numbered) for receiving the storing means 240 is formed between the outer surface of the breathing pipe 220 and the inner surface of the first outer tube 260. The heating device 230 is received in the inner of the breathing pipe 220 for atomizing the tobacco bar received in the storing means 240.

In other embodiments, the first connector 30 may be mounted at one end of the battery assembly 10, the end is closed to the atomizer assembly 20. Accordingly, the second connector 40 may be mounted at one end of the atomizer assembly 20, the end is closed to the battery assembly 10.

A first top electrode 310a and a second top electrode 310b are fixed on the end face of the first connector 30. The first and second top electrodes 310a, 310b extends in the direction toward the second connector 40 along an axial direction of the first connector 30. The first and second top electrodes 310a, 310b are arranged parallelly and spaced from each other. A first bottom electrode 411a and a second bottom electrode 411b are located in the second connector 40 with respect to the first and second top electrodes 310a, 310b. Elastic tight fit may occur between the first top electrode 310a and the first bottom electrode 411a as well as between the second top electrode 310b and the second bottom electrode 411b. In the embodiment, the first and second top electrodes 310a, 310b or the first and second bottom electrodes 411a, 411b are made of elastic conductive material, which can expand or contract in the radial direction of the electrodes. Preferably, the elastic conductive material may be elastic metal.

In the embodiment, the first and second top electrodes 310a, 310b have a same shape and same size, which are connected to two ends of the heating device 230 respectively. The first and second bottom electrodes 411a, 411b have a same shape and same size, but opposite polarity. In the other embodiments, the first and second top electrodes 310a, 310b may have a different shape and different size. Accordingly, the first and second bottom electrodes 411a, 411b may have a different shape and different size.

In the embodiment, the first and second top electrodes 310a, 310b are cylinder shaped, of which the cross section is round shaped or oval shaped. In other embodiments, the cross section of the first and second top electrodes 310a, 310b may be square shaped, triangle shaped, or the like. The first and second bottom electrode 411a, 411b are shaped to match the first and second top electrode 310a, 310b respectively.

Figure 3:
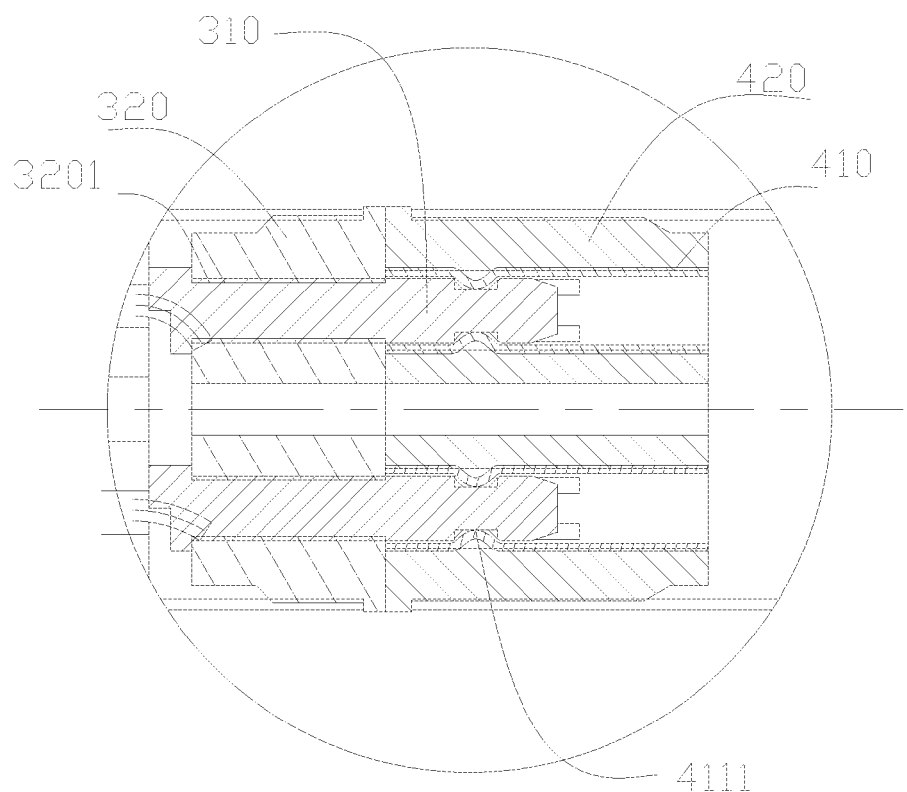
FIG. 3 is an enlarged view of part A in FIG. 2 in accordance with the disclosure.
Figure 4:
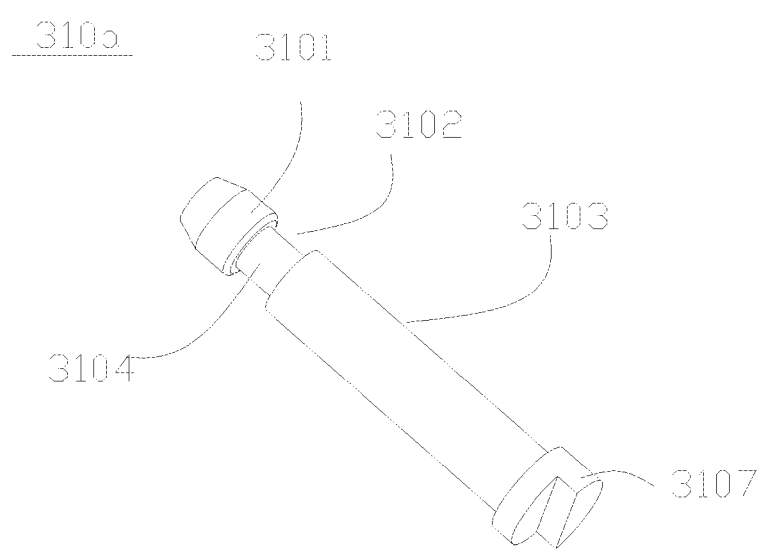
FIG. 4 is a structural view of a top electrode in FIG. 2.
Figure 5:
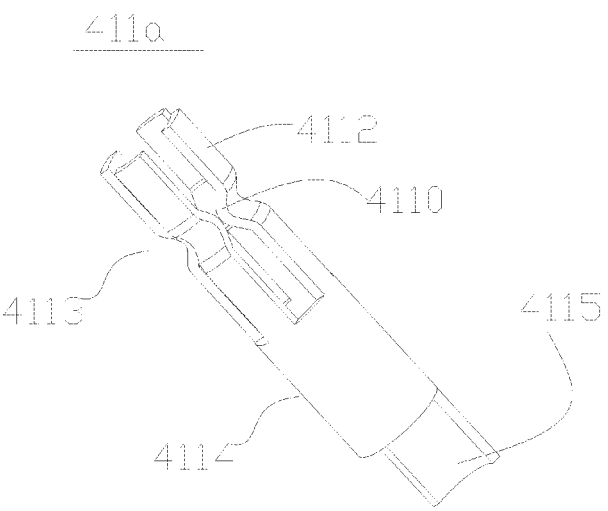
FIG. 5 is a structural view of a bottom electrode in FIG. 2.
Figure 6:
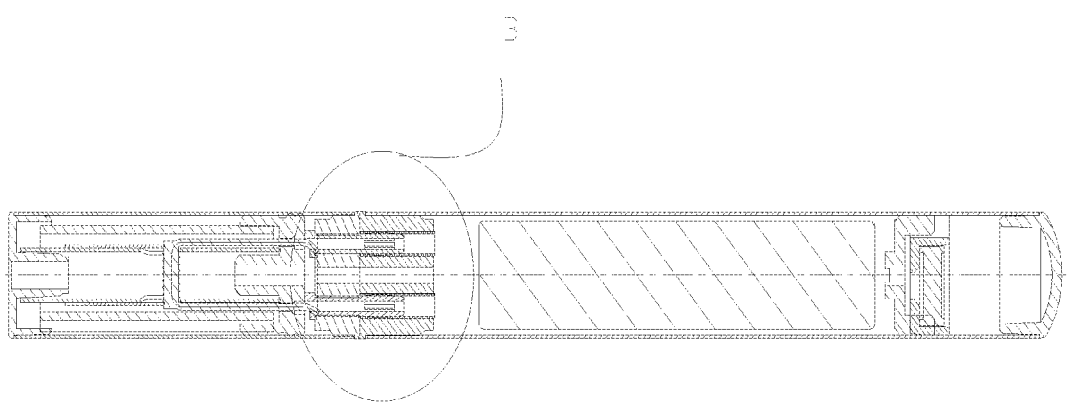
FIG. 6 is a cutaway view of an electronic cigarette in accordance with another embodiment of the disclosure.
Figure 7:
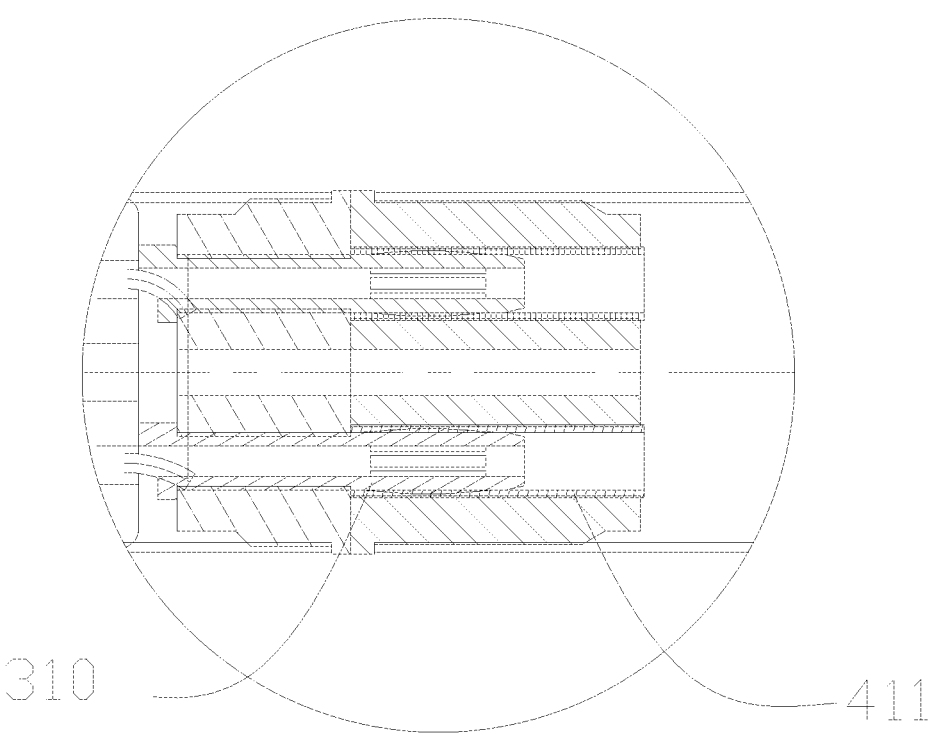
FIG. 7 is an enlarged view of part B in FIG. 6.
Figure 8:
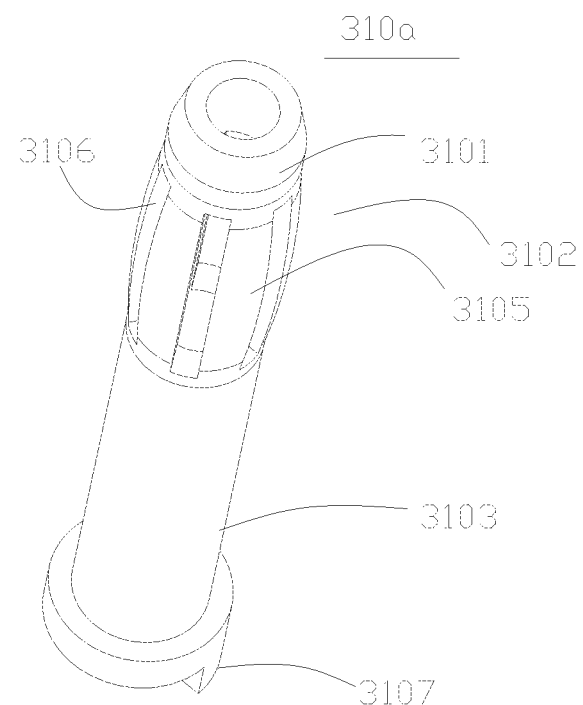
FIG. 8 is a structural view of a top electrode in FIG. 6.
Figure 9:
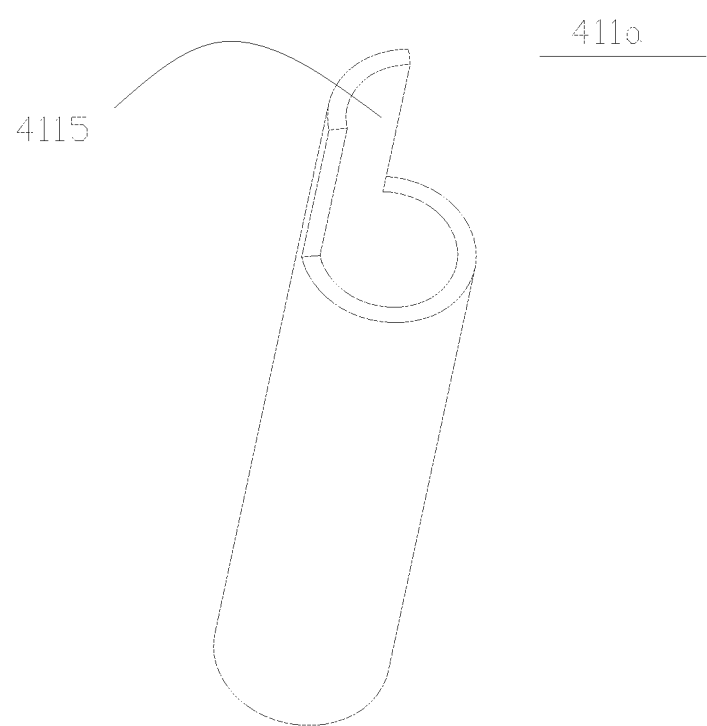
FIG. 9 is a structural view of a bottom electrode in FIG. 6.

As shown in FIG. 3 to FIG. 5, in the embodiment, the cross section of the first top electrode 310a is round shaped. The first top electrode 310a comprises a top part 3101, a connecting part 3102 and a fixing part 3103. The top part 3101 is received in the inner of the first bottom electrode 411a. The connecting part 3102 is connected between the top part 3101 and the fixing part 3103. A diameter of the connecting part 3102 is less than that of the top part 3101 as well as the fixing part 3103, a ring-shaped groove 3104 for engaging with the first bottom electrode 411a is formed on an outer surface of the connecting part 3102. The fixing part 3103 is fixed on the first connector 30. In the embodiment, the first connector 30 includes a first installation base 320. The installation base 320 defines a pair of first installation holes 3201 for fixing the first and second top electrodes 310a, 310b respectively. The first and second top electrodes 310a, 310b are inserted in the pair of installation holes 3201 for being fixed on the first connector 30. Preferably, the first installation base 320 is made of insulative material. The fixing part 3103 of the first top electrode 310a includes a first touching plate 3107, which extends in the direction backward the top part 3101 along the axial direction of the first top electrode 310a. The first touching plate 3107 is connected to the heating device 230 electrically. The first installation base 320 also defines a first breathing hole 311 located between the pair of installation holes 3201. In the embodiment, the second top electrode 310b has a same structure as the first top electrode 310a, which also is made of the same material as the first top electrode 310a. Thus, it is no need to describe the second top electrode 310b in detail again.

In the embodiment, the second connector 40 includes a second installation base 420. The second installation base 420 defines a pair of second installation holes 410 of cylinder-shape for fixing the first and second bottom electrode 411a, 411b. The first bottom electrode 411a includes an engaging part 4113 and a second connecting part 4114 inserted into the installation hole 410. The engaging part 4113 extends in the direction toward the first connector 30. The engaging part 4113 includes a plurality of plates 4112 (divergent electrode plates) arranged radially along the circumferential direction of the engaging part 4113. Each plate 4112 is provided with a protruding part 4110 protruding toward the center line of the second installation hole 410 along the radial direction of the second installation hole 410. The protruding part 4110 may expand and contract in the radial direction of the second installation hole 410. All of the protruding parts 4110 surround to form a block button 4111 for engaging with the ring-shaped groove 3104 of the first top electrode 310a. In the embodiment, the first bottom electrode 411a is made of elastic metal. In such case, the protruding part 4110 can produce elastic deformation in the radial direction of the second installation hole 410 for engaging with the ring-shaped groove 3104 reliably. The second connecting part 4114 of the first bottom electrode 411a is provided with a second touching plate 4115, which extends in the direction that is away from the engaging part 4113 along the axial direction of the second installation hole 410. The second touching part 4115 is electrically connected to the battery 120. The second installation base 420 further defines second breathing hole 412 located between the pair of second installation holes 410. The first breathing hole 311 and the second breathing hole 412 are in coaxial. The first breathing hole 311 communicates with the second breathing hole 412 to form a channel for cigarette smoke flowing, which also communicate with the breathing pipe 220. The second installation base 420 is made of insulative material, such as plastic rubber, or the like. In the embodiment, the second bottom electrode 411b has the same structure as the first bottom electrode 411a, which also is made of the same material as that of the first bottom electrode 411b. Thus, it is no need to describe the second bottom electrode 411b in detail again.

Further, the working principle of the embodiment is described as following:

During assembling of the electronic cigarette, inserts the atomizer assembly 20 into the battery assembly 10. Specifically, inserts the first top electrode 310a into the first bottom electrode 411a as well as inserting the second electrode 310b into the second bottom electrode 411b. The top parts 3101 of the first and second top electrodes 310a, 310b are received in the engaging parts 4113 of the first and second bottom electrode 411a, 411b respectively. Then, the top parts 3101 continue to enter into the engaging parts 4113 so that the block buttons 4111 of the engaging parts 4113 is expanded and produces elastic deformation, which would make the top parts 3101 run through the block buttons 4111. Then, the ring shaped grooves 3104 of the first top electrode 310a and the second top electrode 310b are located in the block buttons 4111. The elastic deformation of the block buttons 4111 recover because the diameters of the connecting parts 3102 are less than that of the top parts 3101 and fixing parts 3103. Therefore, the ring-shaped grooves 3104 are engaged with the block buttons 4111. The elastic tight fit can respectively occur between the ring-shaped grooves 3104 and the block buttons 4111. Further, the first and second top electrodes 310a, 310b and the first and second bottom electrodes 411a, 411b are electrically connected to each other to supply an electrical power for the atomizer assembly 20.

As shown in FIG. 6 to FIG. 9, another embodiment is provided in the disclosure. The difference between the embodiment and the aforementioned embodiment is that the shape of the first and second top electrodes and the first and second bottom electrodes in the embodiment are different from that in the aforementioned embodiment. In the embodiment, the first top electrode 310a includes a top part 3101, a connecting part 3102 and a fixing part 3103. Wherein, the shape of the top part 3101 and fixing part 3103 are the same as that in the aforementioned embodiment. But the shape of the connecting part 3102 is different from that in the aforementioned embodiment. In the embodiment, the connecting part 3102 includes a plurality of protruding strips 3105 and slots 3106 formed between each two adjacent protruding strips 3105. The protruding strips 3105 are arranged along the axial direction of the first top electrode 310a, which can expand and contract in the radial direction of the first top electrode 310a. All of the protruding strips 3105 surround to form the connecting part 3102 of cylinder shape. The diameter of the connecting part 3102 is more than the top part 3101 and the fixing part 3103. In the embodiment, the first top electrode 310a has the same first touching plate 3107 as that in the aforementioned embodiment. In the embodiment, the second top electrode 310b has a same structure as the first top electrode 310a, which also is made of the same material as the first top electrode 310a. Thus, it is no need to describe the second top electrode 310b in detail again. Accordingly, the second installation base 420 of the second connector 40 defines a pair of second installation holes 410 of cylinder-shape for fixing the first and second bottom electrode 411a and 411b. The first bottom electrode 411a received in one of the second installation holes 410 is of hollow cylinder-shape. The diameter of the first bottom electrode 411a is equal to that of the top part 3101 of the first top electrode 310a. In the embodiment, the first top electrode 310a is made of elastic metal. In such case, the elastic tight fit may occur between the first top electrode 310a and the first bottom electrode 411a. In the embodiment, the first bottom electrode 411a also has the second touching plate 4115 as same as that in the aforementioned embodiment. In the embodiment, the second bottom electrode 411b has the same structure as the first bottom electrode 411a, which also is made of the same material as that of the first bottom electrode 411b. Thus, it is no need to describe the second bottom electrode 411b in detail again (referring to FIG. 1 or FIG. 3.)

Further, the working principle of the embodiment is described as following:

During assembling of the electronic cigarette, inserts the atomizer assembly 20 into the battery assembly 10. Specifically, inserts the first top electrode 310a into the hollow inner of the first bottom electrode 411a as well as inserting the second electrode 310b into the hollow inner of the second bottom electrode 411b. Then, the top parts 3101 continue to enter into the hollow inner of the first and second bottom electrodes 411a, 411b. In such case, because of the diameter of the first and second bottom electrodes 411a, 411b equal to that of the top parts 3101 respectively, the connecting parts 3102 are compressed and produce elastic deformation while located in the hollow inner of the first and second bottom electrodes 411a, 411b. The elastic tight fit may respectively occur between the connecting parts 3102 and the first and second bottom electrode 411a and 411b because the connecting parts 3102 generate recover force of the elastic deformation. Further, the first and second top electrodes 310a, 310b and the first and second bottom electrodes 411a, 411b are electrically connected to each other to supply an electrical power for the atomizer assembly 20.

In this disclosure, the atomizer assembly is connected to the battery assembly by means of elastic tight fit occurred between the top electrodes and the bottom electrodes respectively. In such case, the atomizer assembly and the battery assembly can be connected to each other conveniently with less force. While connecting, users only need to insert the atomizer assembly into the battery assembly. In such case, the atomizer assembly and the battery assembly can be connected to each other reliably, which can bring with a good users' feel.

While the present invention has been described by reference to preferred embodiments, it will be understood by those skilled in the art that various changes may be made and equivalents may be substituted without departing from the scope of the present invention. However, all the changes will be included within the scope of the appended claims.

What is claimed is:

1. An electronic cigarette comprising a battery assembly and an atomizer assembly, the battery assembly and the atomizer assembly are connected to each other through a first connector and a second connector,
wherein the first connector comprises a first top electrode and a second top electrode mounted at an end face of the first connector and extending in the direction toward the second connector along an axial direction of the first connector; the first top electrode and the second electrode are arranged parallelly and spaced from each other;
the second connector comprises a first bottom electrode and a second bottom electrode that are located in the second connector with respect to the first and second top electrodes; when the battery assembly and the atomizer assembly are connected together, there are elastic tight fit occurred between the first top electrode and the first bottom electrode as well as between the second top electrode and the second bottom electrode;
the first top electrode and the first bottom electrode are connected electrically to each other, and the second top electrode and the second bottom electrode are connected electrically to each other;
the first top electrode is shaped to be inserted into the first bottom electrode and the second top electrode is shaped to be inserted into the second bottom electrode; both the first and second bottom electrodes are configured to expand and generate elastic deformation so that the atomizer assembly is connected to the battery assembly in the form of elastic tight fit to supply an electric power for the atomizer assembly;
cross sections of the first and second top electrodes are round-shaped; each of the first and second top electrodes comprise a top part, a fixing part and a connecting part; the fixing part is connected to the first connector and the connecting part is connected between the top part and the fixing part; and
a diameter of the connecting part is smaller than that of the top part and the fixing part, and a ring-shaped groove is formed on an outer surface of the connecting part.

2. The electronic cigarette of claim 1, wherein the first top electrode, the second top electrode, the first bottom electrode and the second bottom electrode are made of elastic conductive material that can expand or contract in the radial direction of the electrodes.

3. The electronic cigarette of claim 2, wherein the elastic conductive material is elastic metal.

4. The electronic cigarette of claim 1, wherein the first and second bottom electrodes are of the same shape, each of the first and second bottom electrodes comprise an engaging part extending in the direction toward the first connector and a second connecting part received in the second connector; wherein, the engaging part includes a plurality of plates arranged radially along the circumferential direction of the engaging part; a protruding part that can expand and contract along the radial direction of the engaging part is formed on each plate along the radial direction of the engaging part; all of the protruding parts surround to form a block button for engaging with the ring-shaped groove.

5. The electronic cigarette of claim 4, wherein the first and second bottom electrodes are made of elastic metal.

6. The electronic cigarette of claim 1, wherein the first connector further comprises an first installation base for fixing the first and second top electrodes, the first installation base defines a pair of first installation holes for the installation of the first and second top electrodes, and a first breathing hole is formed between the pair of the first installation holes.

7. The electronic cigarette of claim 6, wherein, the second connector further comprises a second installation base, the second installation base defines a pair of second installation holes for the installation of the first and second bottom electrodes, and a second breathing hole is formed between the pair of the second installation holes, the first breathing hole and the second breathing hole communicate with each other to form a channel for cigarette smoke flowing.

8. The electronic cigarette of claim 7, wherein the first and second installation bases are made of insulated material.

9. The electronic cigarette of claim 1, wherein the atomizer assembly is provided with a first outer tube and the battery assembly is provided with a second outer tube, the first connector or the second connector are mounted at one end of the first outer tube or the second outer tube respectively, the first outer tube is detachably connected to the second outer tube through the connection between the first connector and the second connector.

10. An electronic cigarette comprising a battery assembly and an atomizer assembly, the battery assembly and the atomizer assembly are connected to each other through a first connector and a second connector,
wherein the first connector comprises a first top electrode and a second top electrode mounted at an end face of the first connector and extending in the direction toward the second connector along an axial direction of the first connector; the first top electrode and the second electrode are arranged parallelly and spaced from each other;

the second connector comprises a first bottom electrode and a second bottom electrode that are located in the second connector with respect to the first and second top electrodes; when the battery assembly and the atomizer assembly are connected together, there are elastic tight fit occurred between the first top electrode and the first bottom electrode as well as between the second top electrode and the second bottom electrode;

the first top electrode and the first bottom electrode are connected electrically to each other, and the second top electrode and the second bottom electrode are connected electrically to each other;

the first top electrode is shaped to be inserted into the first bottom electrode and the second top electrode is shaped to be inserted into the second bottom electrode; both the first and second bottom electrodes are configured to expand and generate elastic deformation so that the atomizer assembly is connected to the battery assembly in the form of elastic tight fit to supply an electric power for the atomizer assembly;

cross sections of the first and second top electrodes are round-shaped; each of the first and second top electrodes comprise a top part, a fixing part and a connecting part; the fixing part is connected to the first connector and the connecting part is connected between the top part and the fixing part; and the connecting part comprises a plurality of protruding strips and slots formed between each two adjacent protruding strips, and a diameter of the connecting part is larger than that of the top part.

11. The electronic cigarette of claim 10, wherein, the first and second bottom electrodes are hollow cylinder shaped, and diameters of the first and second bottom electrodes are equal to that of the top parts of the first and second top electrodes.

12. The electronic cigarette of claim 11, wherein the first and second top electrodes are made of elastic metal.

* * * * *